United States Patent
Harada et al.

(10) Patent No.: US 9,862,677 B2
(45) Date of Patent: Jan. 9, 2018

(54) COMPOUND HAVING POLYMERIZABLE GROUP AND CROSSLINKABLE GROUP AND METHOD FOR PRODUCING THE SAME

(71) Applicant: NISSAN CHEMICAL INDUSTRIES, LTD., Tokyo (JP)

(72) Inventors: Yoshikazu Harada, Funabashi (JP); Mitsumasa Kondo, Funabashi (JP); Shojiro Yukawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/128,399

(22) PCT Filed: Mar. 23, 2015

(86) PCT No.: PCT/JP2015/058729
§ 371 (c)(1),
(2) Date: Sep. 22, 2016

(87) PCT Pub. No.: WO2015/146905
PCT Pub. Date: Oct. 1, 2015

(65) Prior Publication Data
US 2017/0107176 A1    Apr. 20, 2017

(30) Foreign Application Priority Data
Mar. 25, 2014 (JP) .................. 2014-061914

(51) Int. Cl.
| C07C 261/00 | (2006.01) |
| C07C 271/16 | (2006.01) |
| C07C 271/20 | (2006.01) |
| C07C 269/02 | (2006.01) |
| C07C 269/06 | (2006.01) |

(52) U.S. Cl.
CPC .......... C07C 271/16 (2013.01); C07C 269/02 (2013.01); C07C 269/06 (2013.01); C07C 271/20 (2013.01)

(58) Field of Classification Search
CPC ... C07C 271/16; C07C 271/20; C07C 269/02; C07C 269/06
See application file for complete search history.

(56) References Cited

U.S. PATENT DOCUMENTS 4,250,322 A * 2/1981 Efimov .................. C08F 20/36
560/115

FOREIGN PATENT DOCUMENTS

| CN | 101983959 A | 3/2011 |
| DE | 2632733 A1 | 1/1978 |
| JP | S53-34892 A | 3/1978 |
| JP | H09-111153 A | 4/1997 |
| JP | 2013-210513 A | 10/2013 |
| WO | 2015/056741 A1 | 4/2015 |
| WO | WO2015056741 | * 4/2015 |
| WO | WO2016143860 | * 9/2016 |
| WO | WO2016143865 | * 9/2016 |

OTHER PUBLICATIONS

May 26, 2015 International Search Report issued in International Patent Application No. PCT/JP2015/058729.
May 26, 2015 Written Opinion of the International Searching Authority issued in International Patent Application No. PCT/JP2015/058729.

* cited by examiner

Primary Examiner — Yevegeny Valenrod
Assistant Examiner — Blaine G Doletski
(74) Attorney, Agent, or Firm — Oliff PLC

(57) ABSTRACT

An acrylic or methacrylic compound having N-alkoxyalkyl group; and a method for producing the compound. An acrylic or methacrylic compound having N-alkoxyalkyl group, of Formula [1]:

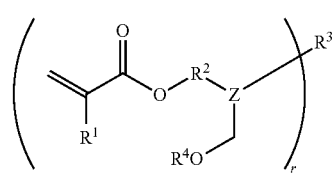

[1]

[where $R^1$ is a hydrogen atom or methyl group; $R^2$ is a $C_{2-20}$ alkylene group etc.; $R^3$ is an r-valent $C_{2-20}$ aliphatic group etc.; $R^4$ is a $C_{1-20}$ alkyl group etc.; Z is >NCOO— or —OCON< (where "-" is a bond, ">" and "<" each have two bonds, and any one of ">" and "<" is bonded to —$CH_2OR^4$); and r is a natural number of 2 or more and 9 or less].

10 Claims, No Drawings

COMPOUND HAVING POLYMERIZABLE GROUP AND CROSSLINKABLE GROUP AND METHOD FOR PRODUCING THE SAME

TECHNICAL FIELD

The present invention relates to a compound having a polymerizable group and a crosslinkable group and a method for producing the same, and in particular, an acrylic or methacrylic compound having N-alkoxyalkyl group and a method for producing the same.

BACKGROUND ART

In recent years, in fields of displays such as televisions using a liquid crystal panel, and semiconductors, application of patterning by applying a certain resin composition to a substrate followed by irradiation with light is increased. For achieving high efficiency and improved mechanical properties, a low molecular compound is added to such a resin composition to increase the sensitivity to ultraviolet light, and increase the hardness of a film.

Examples of such a low molecular compound include an acrylic compound having only one N-alkoxyalkyl group and one acrylic group in one molecule. Specific examples thereof include N-methoxymethylacrylamide. N-methoxymethylacrylamide is used in a wide range of fields as an adhesive component for optical materials described in Patent Document 1 or a reactive monomer for modification of fibers and resins described in Patent Document 2.

PRIOR ART DOCUMENTS

Patent Documents

Patent Document 1: Japanese Patent Application Publication No. 2013-210513 (JP 2013-210513 A)
Patent Document 2: Japanese Patent Application Publication No. 1997-111153 (JP 1997-111153 A)

SUMMARY OF THE INVENTION

Problem to be Solved by the Invention

When a resin composition is applied to a substrate, a procedure in which a cross-linking agent and a low molecular compound to be reacted with the cross-linking agent are introduced into the resin composition to form a strong network and enhance the function of cured film is often used. However, when the low molecular compound does not have a light-reactive group, there are problems in which sufficient properties cannot be imparted to the cured film after a step of irradiation with light, peeling caused by film strength appears, and the deterioration rate is high.

In general, since a compound having an aromatic ring has ultraviolet light-absorption power, the compound absorbs light energy to inhibit light patterning. Further, the transparency of the cured film may be deteriorated by coloration due to an oxidation reaction. Thus, the compound is not preferred.

Means for Solving the Problems

The present inventors have intensively studied to solve the above-described problems, and as a result, found a method for producing a compound having a plurality of acrylic or methacrylic groups as light-reactive groups in one molecule and having a plurality of N-alkoxyalkyl groups as crosslinkable groups. Thus, the present invention has been accomplished. Specifically, the present invention relates to the following first and second aspects.

A first aspect of the present invention relates to an acrylic or methacrylic compound having N-alkoxyalkyl group, of Formula [1]:

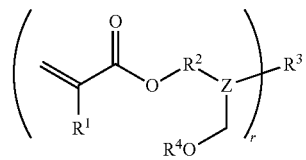

[where
$R^1$ is a hydrogen atom or methyl group;
$R^2$ is a $C_{2-20}$ alkylene group, a divalent group consisting of a $C_{5-6}$ aliphatic ring, or a divalent aliphatic group containing a $C_{5-6}$ aliphatic ring, the group optionally containing an ether bond in its structure and the alkylene group being optionally linear or branched;
$R^3$ is an r-valent $C_{2-20}$ aliphatic group, an r-valent group consisting of a $C_{5-6}$ aliphatic ring, or an r-valent aliphatic group containing a $C_{5-6}$ aliphatic ring, the group optionally containing an ether bond in its structure and the r-valent $C_{2-20}$ aliphatic group being optionally linear or branched;
$R^4$ is a $C_{1-20}$ alkyl group, a monovalent group consisting of a $C_{5-6}$ aliphatic ring, or a monovalent aliphatic group containing a $C_{5-6}$ aliphatic ring, the group optionally containing an ether bond in its structure and the alkyl group being optionally linear or branched;
Z is >NCOO— or —OCON< (where "-" is a bond, ">" and "<" each have two bonds, and any one of ">" and "<" is bonded to —$CH_2OR^4$); and
r is a natural number of 2 or more and 9 or less].

In the first aspect of the present invention, it is preferable that $R^2$ be a $C_{2-10}$ alkylene group, a divalent group consisting of a $C_{5-6}$ aliphatic ring, or a divalent aliphatic group containing a $C_{5-6}$ aliphatic ring, the group optionally containing an ether bond in its structure and the alkylene group being optionally linear or branched;
$R^3$ be an r-valent $C_{2-10}$ aliphatic group, an r-valent group consisting of a $C_{5-6}$ aliphatic ring, or an r-valent aliphatic group containing a $C_{5-6}$ aliphatic ring, the group optionally containing an ether bond in its structure and the r-valent $C_{2-20}$ aliphatic group being optionally linear or branched;
$R^4$ be a linear or branched $C_{1-6}$ alkyl group; and
r be 2 to 6.

In the first aspect of the present invention, it is preferable that $R^4$ be methyl group, ethyl group, n-propyl group, or n-butyl group.

In the first aspect of the present invention, it is preferable that $R^2$ be ethylene group.

In the first aspect of the present invention, it is preferable that $R^3$ be n-hexylene group and r be 2.

A second aspect of the present invention relates to a method for producing an acrylic or methacrylic compound having N-alkoxyalkyl group of Formula [1]:

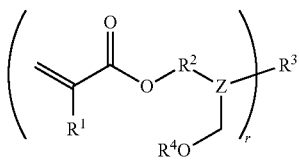

[where $R^1$, $R^2$, $R^3$, $R^4$, and r each have the meanings described below, Z is >NCOO— or —OCON< (where "-" is a bond, ">" and "<" each have two bonds, and any one of ">" and "<" is bonded to —CH$_2$OR$^4$)], comprising reacting a compound of Formula (A):

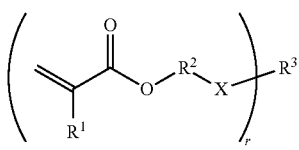

[where
$R^1$ is a hydrogen atom or methyl group;
$R^2$ is a $C_{2-20}$ alkylene group, a divalent group consisting of a $C_{5-6}$ aliphatic ring, or a divalent aliphatic group containing a $C_{5-6}$ aliphatic ring, the group optionally containing an ether bond in its structure and the alkylene group being optionally linear or branched;
$R^3$ is an r-valent $C_{2-20}$ aliphatic group, an r-valent group consisting of a $C_{5-6}$ aliphatic ring, or an r-valent aliphatic group containing a $C_{5-6}$ aliphatic ring, the group optionally containing an ether bond in its structure and the r-valent $C_{2-20}$ aliphatic group being optionally linear or branched;
X is —NHCOO— or —OCONH—; and
r is a natural number of 2 or more and 9 or less] with paraformaldehyde and trimethylsilyl chloride, and reacting the product with an alcohol compound of Formula (G):

R$^4$—OH    (G)

(where $R^4$ is a $C_{1-20}$ alkyl group, a monovalent group consisting of a $C_{5-6}$ aliphatic ring, or a monovalent aliphatic group containing a $C_{5-6}$ aliphatic ring, the group optionally containing an ether bond in its structure and the alkyl group being optionally linear or branched).

In the second aspect of the present invention, it is preferable that $R^2$ be a $C_{2-10}$ alkylene group, a divalent group consisting of a $C_{5-6}$ aliphatic ring, or a divalent aliphatic group containing a $C_{5-6}$ aliphatic ring, the group optionally containing an ether bond in its structure and the alkylene group being optionally linear or branched;
$R^3$ be an r-valent $C_{2-10}$ aliphatic group, an r-valent group consisting of a $C_{5-6}$ aliphatic ring, or an r-valent aliphatic group containing a $C_{5-6}$ aliphatic ring, the group optionally containing an ether bond in its structure and the r-valent $C_{2-20}$ aliphatic group being optionally linear or branched;
$R^4$ be a linear or branched $C_{1-6}$ alkyl group; and
r be 2 to 6.

In the second aspect of the present invention, it is preferable that $R^4$ be methyl group, ethyl group, n-propyl group, or n-butyl group.

In the second aspect of the present invention, it is preferable that $R^2$ be ethylene group.

In the second aspect of the present invention, it is preferable that $R^3$ be n-hexylene group and r be 2.

Effects of the Invention

According to the compound of the present invention, the adhesion of a cured film obtained from a resin composition to a liquid crystal can be improved.

When the compound of the present invention is used for the resin composition, durability such as heat resistance and water resistance can be imparted to the cured film. Since the compound is a compound containing no aromatic ring, the cured film is unlikely to be colored, and the transparency of the cured film can be maintained.

The compound of the present invention can be expected to further improve a film curing property by a cross-linking effect after a step of irradiation with light.

According to the production method of the present invention, the acrylic or methacrylic compound having N-alkoxyalkyl group, of Formula [1] described above, can be efficiently produced.

MODES FOR CARRYING OUT THE INVENTION

Hereinafter, the present invention will be described in detail. Herein, "n" means normal, "i" means iso, "s" means secondary, and "t" means tertiary.

The present invention relates to a compound having a plurality of acrylic or methacrylic groups as light-reactive groups in one molecule and having a plurality of N-alkoxyalkyl groups as crosslinkable groups. Specifically, the present invention relates to an acrylic or methacrylic compound having N-alkoxyalkyl group of Formula [1] (hereinafter abbreviated to compound 1).

The compound 1 of the present invention has a plurality of acrylic or methacrylic groups as light-reactive groups in one molecule and having a plurality of N-alkoxyalkyl groups as crosslinkable groups. Therefore, a tight cross-linking network can be formed in a cured film to be formed from a resin composition, and the compound 1 can contribute to improved adhesion and durability.

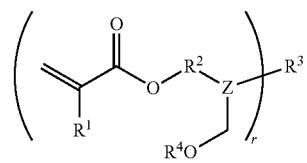

[where
$R^1$ is a hydrogen atom or methyl group;
$R^2$ is a $C_{2-20}$ alkylene group, a divalent group consisting of a $C_{5-6}$ aliphatic ring, or a divalent aliphatic group containing a $C_{5-6}$ aliphatic ring, the group optionally containing an ether bond in its structure and the alkylene group being optionally linear or branched;
$R^3$ is an r-valent $C_{2-20}$ aliphatic group, an r-valent group consisting of a $C_{5-6}$ aliphatic ring, or an r-valent aliphatic group containing a $C_{5-6}$ aliphatic ring, the group optionally containing an ether bond in its structure and the r-valent $C_{2-20}$ aliphatic group being optionally linear or branched;

$R^4$ is a $C_{1-20}$ alkyl group, a monovalent group consisting of a $C_{5-6}$ aliphatic ring, or a monovalent aliphatic group containing a $C_{5-6}$ aliphatic ring, the group optionally containing an ether bond in its structure and the alkyl group being optionally linear or branched;

Z is >NCOO— or —OCON< (where "-" is a bond, ">" and "<" each have two bonds, and any one of ">" and "<" is bonded to —$CH_2OR^4$); and r is a natural number of 2 or more and 9 or less].

Specific examples of the $C_{2-20}$ alkylene group in the definition of $R^2$ include a divalent group obtained by removing one hydrogen atom from a $C_{2-20}$ alkyl group.

Specific examples of the r-valent $C_{2-20}$ aliphatic group in the definition of $R^3$ include an r-valent group obtained by further removing one to r-1 hydrogen atoms from a $C_{2-20}$ alkyl group.

Specific examples of the $C_{2-20}$ alkyl group include ethyl group, n-propyl group, i-propyl group, n-butyl group, i-butyl group, s-butyl group, t-butyl group, n-pentyl group, 1-methyl-n-butyl group, 2-methyl-n-butyl group, 3-methyl-n-butyl group, 1,1-dimethyl-n-propyl group, n-hexyl group, 1-methyl-n-pentyl group, 2-methyl-n-pentyl group, 1,1-dimethyl-n-butyl group, 1-ethyl-n-butyl group, 1,1,2-trimethyl-n-propyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, cyclopentyl group, cyclohexyl group, and a group in which one or more thereof are bonded such that the carbon atom number is 20 or less. One example of the groups is a group in which one methylene group of the groups or a plurality of methylene groups that are not adjacent are substituted with an ether bond, or the like.

In particular, it is preferable that $R^2$ be a $C_{2-10}$ alkylene group and $R^3$ be an r-valent $C_{2-10}$ aliphatic group, and more preferably an r-valent $C_{2-10}$ alkyl group. It is particularly preferable that $R^2$ be ethylene group and $R^3$ be n-hexylene group in terms of acquisition of raw materials and the like.

Specific examples of the $C_{1-20}$ alkyl group in the definition of $R^4$ include specific examples of the $C_{2-20}$ alkyl group in the description of definition of $R^2$ and methyl group. Among these groups, it is preferable that $R^4$ be a linear or branched $C_{1-6}$ alkyl group, and particularly preferably methyl group, ethyl group, n-propyl group, or n-butyl group.

Examples of the divalent group consisting of a $C_{5-6}$ aliphatic ring in the definition of $R^2$ include a divalent group having a structure obtained by removing two hydrogen atoms from a cyclopentyl ring or cyclohexane ring.

Examples of the divalent aliphatic group containing a $C_{5-6}$ aliphatic ring in the definition of $R^2$ include alkylene group containing a cyclopentyl ring or a cyclohexane ring.

Examples of the r-valent group consisting of a $C_{5-6}$ aliphatic ring in the definition of $R^3$ include an r-valent group having a structure obtained by removing r hydrogen atoms from a cyclopentyl ring or a cyclohexane ring.

Examples of the r-valent aliphatic group containing a $C_{5-6}$ aliphatic ring in the definition of $R^3$ include r-valent alkyl group containing a cyclopentyl ring or a cyclohexane ring.

Examples of the monovalent group containing a $C_{5-6}$ aliphatic ring in the definition of $R^4$ include cyclopentyl group and cyclohexyl group.

Examples of the monovalent aliphatic group containing a $C_{5-6}$ aliphatic ring in the definition of $R^4$ include alkyl group containing a cyclopentyl ring or a cyclohexane ring.

r is a natural number of 2 or more and 9 or less. Among the numbers, 2 to 6 are preferred.

The compound 1 can be obtained by a production method of the following reaction scheme. Specifically, a carbamate compound (A) having an acrylic or methacrylic group of Formula (A) (hereinafter also referred to as compound (A)) is reacted in a solvent to which trimethylsilyl chloride and paraformaldehyde are added, to synthesize an intermediate (B) of Formula (B). To the reaction liquid, an alcohol (G) of Formula (G) is added, causing a reaction. Thus, the target compound 1 is produced.

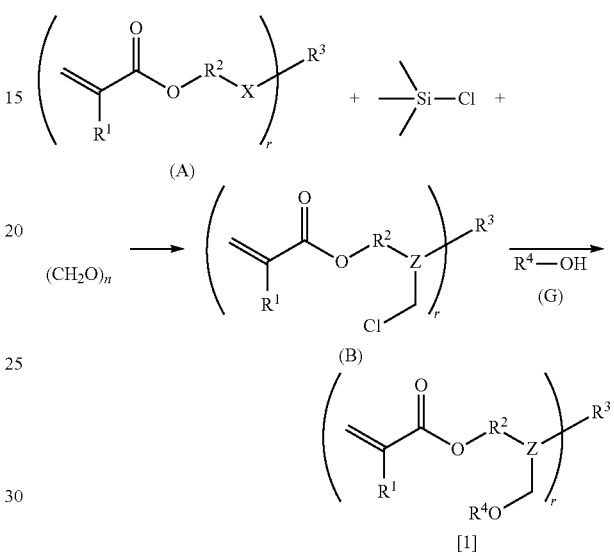

(where $R^1$, $R^2$, $R^3$, $R^4$, Z, and r have the meanings described above, and X is —NHCOO— or —OCONH—.)

The amounts of trimethylsilyl chloride and paraformaldehyde to be used relative to the compound (A) are not particularly limited. In order to complete the reaction, it is preferable that 1.0 to 6.0 equivalents of trimethylsilyl chloride and 1.0 to 3.0 equivalents of paraformaldehyde be used with respect to one carbamate bond in the molecule, and it is more preferable that the equivalents of trimethylsilyl chloride to be used be larger than that of paraformaldehyde.

A reaction solvent is not particularly limited as long as it is inert to the reaction. Examples thereof include hydrocarbons such as hexane, cyclohexane, benzene, and toluene; halogenated hydrocarbons such as methylene chloride, carbon tetrachloride, chloroform, and 1,2-dichloroethane; ethers such as diethyl ether, diisopropyl ether, 1,4-dioxane, and tetrahydrofuran; nitriles such as acetonitrile and propionitrile; nitrogen-containing aprotic polar solvents such as N,N-dimethylformamide, N,N-dimethylacetamide, N-methyl-2-pyrrolidone, and 1,3-dimethyl-2-imidazolidinone; and pyridines such as pyridine and picoline. The solvent may be used singly or two or more thereof may be mixed and used. Methylene chloride and chloroform are preferred, and methylene chloride is further preferable.

The amount (reaction concentration) of the solvent to be used is not particularly limited, and the reaction may be carried out without the solvent. When the solvent is used, it may be used in an amount of 0.1 to 100 times by mass, preferably 1 to 30 times by mass, and more preferably 2 to 20 times by mass the amount of the compound (A).

The reaction temperature is not particularly limited, and is, for example, −90 to 200° C., preferably −20 to 100° C., and more preferably −10 to 50° C.

The reaction time is generally 0.05 to 200 hours, and preferably 0.5 to 100 hours.

The reaction may be carried out under normal pressure or under pressure. The reaction may be carried out in a batch-wise or continuous manner.

During the reaction, a polymerization inhibitor may be added. As such a polymerization inhibitor, 2,6-di-tert-butyl-p-cresol (BHT), hydroquinone, p-methoxyphenol, or the like, can be used. The polymerization inhibitor is not particularly limited as long as it inhibits polymerization of the acrylic group or the methacrylic group.

The amount of polymerization inhibitor to be used is not particularly limited, and is 0.0001 to 10 wt %, and preferably 0.01 to 1 wt %, relative to the total amount (mass) of the compound (A) to be used. Herein, wt % means % by mass.

At the step of reacting the intermediate (B) with the alcohol (G), a base may be added to suppress hydrolysis under an acidic condition. Examples of the base include pyridines such as pyridine and picoline, and tertiary amines such as trimethylamine, triethylamine, diisopropylethylamine, and tributylamine. Triethylamine and diisopropylethylamine are preferred, and triethylamine is more preferred. The addition amount of a base is not particularly limited, and 0.01 to 2.0 equivalents of a base, and more preferably 0.5 to 1.0 equivalents of a base only need to be used with respect to the addition amount of trimethylsilyl chloride used in the reaction.

After the intermediate (B) is obtained from the compound (A), the reaction may be caused by adding the alcohol (G) without isolating the intermediate (B).

A method for synthesizing the compound (A) is not particularly limited. A compound of Formula (A-1) can be produced by reacting an isocyanate compound (C) having an acrylic or methacrylic group of Formula (C) with an alcohol compound (D) having a plurality of hydroxyl groups of Formula (D).

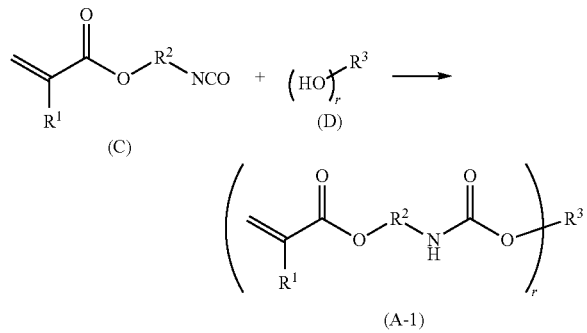

(where $R^1$, $R^2$, $R^3$, and r have the same meanings as described above.)

In this reaction, 0.98 to 1.2 equivalents of the isocyanate compound (C) with respect to one hydroxyl group contained in the compound (D) may be reacted, and more preferably 1.0 to 1.02 equivalents of the isocyanate compound (C).

A reaction solvent is not particularly limited as long as it is inert to the reaction. Examples thereof include hydrocarbons such as hexane, cyclohexane, benzene, and toluene; halogenated hydrocarbons such as carbon tetrachloride, chloroform, and 1,2-dichloroethane; ethers such as diethyl ether, diisopropyl ether, 1,4-dioxane, and tetrahydrofuran; ketones such as acetone, methyl ethyl ketone, and methyl isobutyl ketone; nitriles such as acetonitrile and propionitrile; carboxylic acid esters such as ethyl acetate and ethyl propionate; nitrogen-containing aprotic polar solvents such as N,N-dimethylformamide, N,N-dimethylacetamide, N-methyl-2-pyrrolidone, and 1,3-dimethyl-2-imidazolidinone; sulfur-containing aprotic polar solvents such as dimethyl sulfoxide and sulfolane; and pyridines such as pyridine and picoline. The solvent may be used singly or two or more thereof may be mixed and used. Toluene, acetonitrile, and ethyl acetate are preferred, and toluene and ethyl acetate are more preferred.

The amount (reaction concentration) of the solvent to be used is not particularly limited, and the reaction may be carried out without the solvent. When the solvent is used, it may be used in an amount of 0.1 to 100 times by mass, preferably 0.5 to 30 times by mass, and more preferably 1 to 10 times by mass the amount of the isocyanate compound (C).

The reaction temperature is not particularly limited, and is, for example, −90 to 150° C., preferably −30 to 100° C., and more preferably 0 to 80° C.

The reaction time is generally 0.05 to 200 hours, and preferably 0.5 to 100 hours.

During the reaction, a polymerization inhibitor may be added. As such a polymerization inhibitor, 2,6-di-tert-butyl-p-cresol (BHT), hydroquinone, p-methoxyphenol, or the like, can be used. The polymerization inhibitor is not particularly limited as long as it inhibits polymerization of the acrylic group or methacrylic group.

The amount of polymerization inhibitor to be added is not particularly limited, and is 0.0001 to 10 wt %, and preferably 0.01 to 1 wt %, relative to the total amount (mass) of an acrylic acid ester compound or an methacrylic acid ester compound.

In order to shorten the reaction time, a catalyst may be added. Examples thereof include organotin compounds such as dibutyltin dilaurate, dioctyltin bis(isooctyl thioglycolate), dibutyltin bis(isooctyl thioglycolate), and dibutyltin diacetate; amines such as triethylamine, trimethylamine, tripropylamine, tributylamine, diisopropylethylamine, N,N-dimethylcyclohexylamine, pyridine, tetramethylbutane diamine, N-methylmorpholine, 1,4-diazabicyclo-2.2.2-octane, 1,8-diazabicyclo[5.4.0]undecene, and 1,5-diazabicyclo[4.3.0]nonene-5; organic sulfonic acids such as p-toluenesulfonic acid, methanesulfonic acid, and fluorosulfonic acid; inorganic acids such as sulfuric acid, phosphoric acid, and perchloric acid; titanium compounds such as tetrabutyl titanate, tetraethyl titanate, and tetraisopropyl titanate; bismuth-based compounds such as bismuth tris(2-ethylhexanoate); and quaternary ammonium salts. One catalyst may be used singly or two or more thereof may be used in combination. It is preferable that the catalyst be a liquid or be dissolved in the reaction solvent.

When the catalyst is added, the catalyst may be used in an amount of 0.005 to 100 wt %, preferably 0.05 to 10 wt %, and more preferably 0.1 to 5 wt %, relative to the total amount (mass) of the compound having an isocyanate group to be used. When an organotin compound, a titanium compound, or a bismuth-based compound is used as the catalyst, it is preferable that the amount thereof be 0.005 to 0.1 wt %.

The reaction may be carried out under normal pressure or under pressure. The reaction may be carried out in a batch-wise or continuous manner.

Specific examples of the compound (C) include 2-methacryloyloxyethyl isocyanate (trade name: Karenz MOI (registered trademark), available from Showa Denko K.K.), and 2-acryloyloxyethyl isocyanate (trade name: Karenz AOI (registered trademark), available from Showa Denko K.K.).

Specific examples of the compound (D) include diol compounds such as ethylene glycol, propylene glycol, 1,4-butanediol, 1,3-butanediol, 1,5-pentanediol, neopentyl glycol, 3-methyl-1,5-pentanediol, 1,6-hexanediol, and 1,4-cyclohexanedimethaol, and triol compounds such as glycerin and trimethylolpropane, pentaerythritol, dipentaerythritol, and diglycerin.

The compounds (C) and (D) are generally commercially available or can be synthesized by a publicly known method.

A method for synthesizing a compound of Formula (A-2) is not particularly limited. For example, the compound of Formula (A-2) can be synthesized by reacting a hydroxyalkyl ester compound (E) having an acrylic or methacrylic group of Formula (E) (hereinafter referred to as compound (E)) with a compound (F) having a plurality of isocyanate groups of Formula (F).

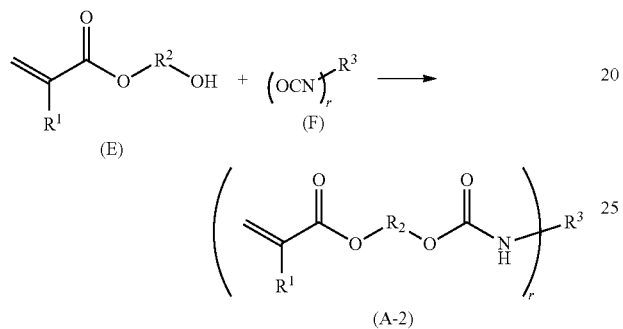

(where $R^1$, $R^2$, $R^3$, and r have the same meanings as described above.)

The compound (A-2) can be synthesized by the same method for synthesizing the compound (A-1). In this reaction, 0.98 to 1.2 equivalents of the compound (E) may be reacted, and more preferably 1.0 to 1.02 equivalents of the compound (E) with respect to one isocyanate group in the isocyanate compound (F).

A reaction condition in this reaction is in accordance with the reaction condition in the production of the compound (A-1).

Specific examples of the compound (E) include monomers having a hydroxy group such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, diethylene glycol monoacrylate, diethylene glycol monomethacrylate, poly(ethylene glycol)ethyl ether acrylate, and poly(ethylene glycol)ethyl ether methacrylate.

Specific examples of the isocyanate compound (F) include aliphatic diisocyanates such as hexamethylene diisocyanate, 2,4,4-trimethylhexamethylene diisocyanate, and dimer acid diisocyanate, alicyclic diisocyanates such as isophorone diisocyanate, 4,4'-methylene bis(cyclohexyl isocyanate), and ω,ω'-diisocyanatedimethylcyclohexane, and triisocyanates such as lysine ester triisocyanate, 1,6,11-undecane triisocyanate, 1,8-diisocyanate-4-isocyanate methyloctane, 1,3,6-hexamethylene triisocyanate, and bicycloheptane triisocyanate.

The compounds (E) and (F) are generally commercially available or can be synthesized by a publicly known method.

The reaction mixture after completion of the reaction is subjected to a general post treatment in which the reaction mixture is directly concentrated, or is dissolved in an organic solvent, washed with water, and then concentrated, or is added to iced water, extracted with an organic solvent, and then concentrated. Thus, the target compounds of the present invention can be obtained. When purification is required, separation or purification can be carried out by any purification method such as recrystallization, column chromatograph, thin-layer chromatograph, and liquid chromatograph separation.

EXAMPLES

Hereinafter, the present invention will be described in more detail with reference to Examples, but the present invention is not limited to Examples.

Abbreviations in Examples and the like each show the following meaning.

CIN1: 6-hydroxyhexyloxy cinnamic acid methyl ester

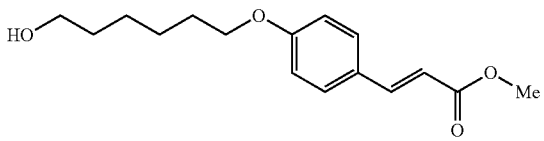 [SMILES: COC(=O)/C=C/c1ccc(OCCCCCCO)cc1]

<Cross-Linking Agent>

HMM: melamine cross-linking agent of the following structural formula

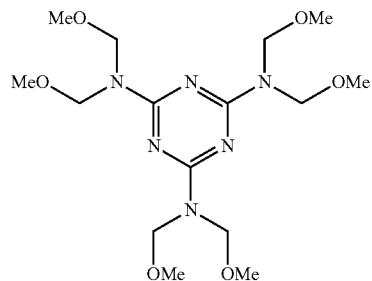 [SMILES: COCN(COC)c1nc(N(COC)COC)nc(N(COC)COC)n1]

<Cross-Linking Catalyst>

PTSA: p-toluenesulfonic acid

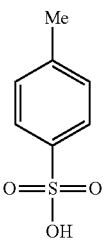

<Compound Having N-Alkoxyalkyl Group and Acrylic Group>

DM-1

[DM-1]

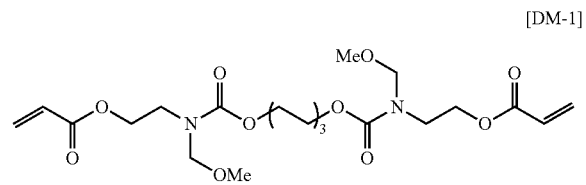

DM-2

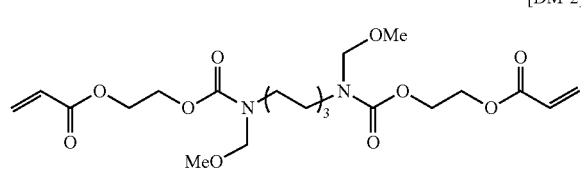

BHT: 2,6-di-tert-butyl-p-cresol
DBU: 1,8-diazabicyclo[5.4.0]-7-undecene

<Solvent>
Each cured film-forming composition of Examples and Comparative Example contained a solvent. As the solvent, propylene glycol monomethyl ether (PGME) was used.

<Measurement of Molecular Weight of Polymer>
The molecular weight of acrylic copolymer in Synthesis Example was measured using a normal temperature gel permeation chromatography (GPC) device (GPC-101) manufactured by Shodex and a column (KD-803 and KD-805) manufactured by Shodex, as described below.

Column Temperature: 50° C.
Eluent: N,N-dimethylformamide (additives: 30 mmol/L lithium bromide monohydrate (LiBr.H$_2$O), 30 mmol/L dehydrated crystal phosphoric acid (o-phosphoric acid), 10 mL/L tetrahydrofuran (THF))
Flow rate: 1.0 mL/min
Standard sample for formation of calibration curve: TSK polyethylene oxide standard available from TOSOH CORPORATION (molecular weight: about 900,000, 150,000, 100,000, 30,000) and polyethylene glycol available from Polymer Laboratories Inc. (molecular weight: about 12,000, 4,000, 1,000).

Note that the number average molecular weight (hereinafter referred to as Mn) and the weight average molecular weight (hereinafter referred to as Mw) are represented as values in terms of polystyrene.

<Measurement of $^1$H-NMR>
An analyzer and analysis used conditions in $^1$H-NMR analysis are as follows:
Nuclear magnetic resonance spectrometer: Varian NMR System 400 NB (400 MHz)
Measurement solvent: CDCl$_3$
Standard material: tetramethylsilane (TMS) (δ 0.0 ppm for $^1$H)

Example 1: Synthesis of Compound [DM-1]

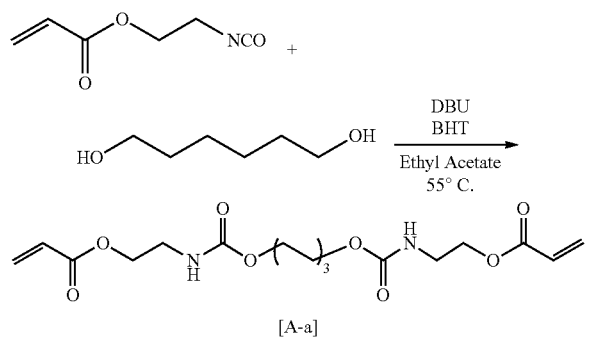

500 g of ethyl acetate, 35.5 g (0.300 mol) of 1,6-hexanediol, 1.80 g (11.8 mmol) of DBU, and 0.45 g (2.04 mmol) of BHT were placed in a 2-L four necked flask under nitrogen flow, and heated to 55° C. with stirring by a magnetic stirrer. To the reaction liquid, 95.9 g (0.679 mol) of 2-isocyanatoethyl acrylate was added dropwise, and the mixture was stirred for 2 hours. The reaction liquid was then analyzed by high performance liquid chromatography. When the area percentage of intermediate reached 1% or less, the reaction was completed. 328 g of hexane was added, and the mixture was cooled to room temperature. The deposited solid was then washed twice with 229 g of hexane, and dried to obtain a compound [A-a] (104 g, 0.260 mol, yield: 86.7%).

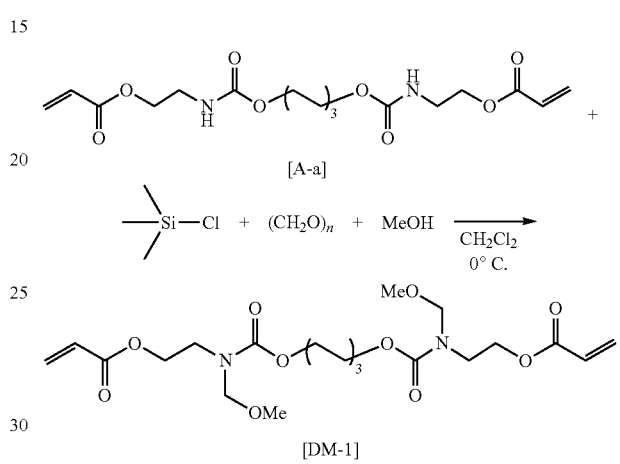

1,330 g of dichloromethane, 100 g (0.250 mol) of the compound [A-a], and 22.5 g (0.749 mol) of paraformaldehyde were placed in a 2-L four necked flask under nitrogen flow, and 122 g (1.12 mol) of trimethylsilyl chloride was added dropwise in an ice bath. The mixture was stirred for 2 hours, and a mixture liquid of 63.2 g (0.625 mol) of triethylamine and 240 g of methanol was added dropwise. The mixture was stirred for 30 minutes, and then put into a 5-L separation funnel. 1,500 g of water was added, and a separation operation was carried out. The obtained organic phase was dried over magnesium sulfate, the magnesium sulfate was removed by filtration, and the obtained filtrate was then concentrated and dried to obtain the compound [DM-1] (110 g, 0.226 mol, yield: 90.3%).

The structure of the compound [DM-1] was confirmed from the following spectral data obtained by $^1$H-NMR analysis.

$^1$H-NMR (CDCl$_3$): δ 6.42 (d, 2H J=17.2), 6.17-6.08 (m, 2H), 5.86 (d, 2H J=10.0), 4.77 (d, 4H J=19.6), 4.30 (m, 4H), 4.12 (t, 4H J=6.4), 3.61 (m, 4H), 3.30 (d, 6H J=12.8), 1.67 (m, 4H), 1.40 (m, 4H).

Example 2: Synthesis of Compound [DM-2]

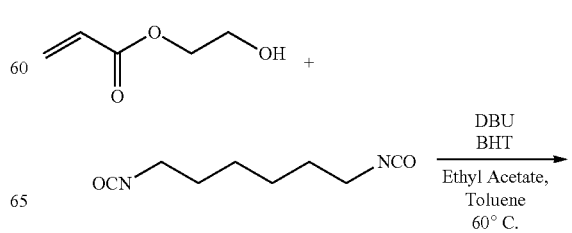

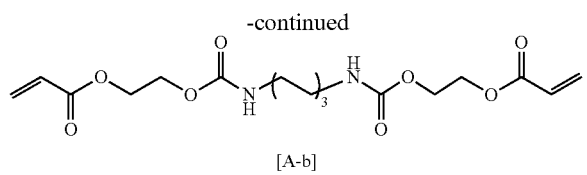

[A-b]

35.0 g of ethyl acetate, 87.0 g of toluene, 8.41 g (50.0 mmol) of hexamethylene diisocyanate, 0.345 g (2.27 mmol) of DBU, and 70.0 mg (0.318 mmol) of BHT were placed in a 500-mL four necked flask under nitrogen flow, and heated to 60° C. with stirring by a magnetic stirrer. To the reaction liquid, a mixed liquid of 12.8 g (111 mmol) of 2-hydroxyethyl acrylate and 26.0 g of toluene was added dropwise, and the mixture was stirred for 1 hour, and then stirred at room temperature for 24 hours. 131 g of hexane was added, and the mixture was cooled in an ice bath. The deposited solid was then filtered and dried to obtain a compound [A-b] (15.0 g, 37.4 mmol, yield: 74.8%).

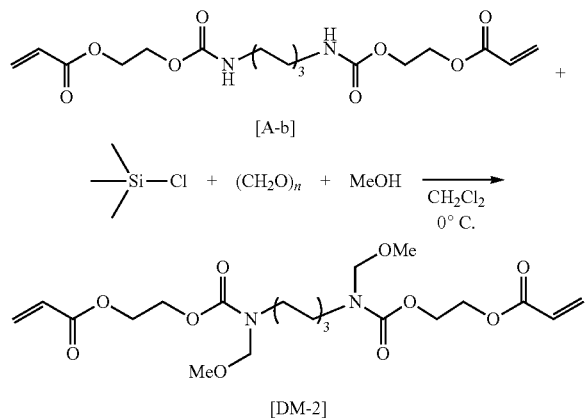

200 g of dichloromethane, 14.6 g (36.4 mmol) of the compound [A-b], and 3.28 g (109 mmol) of paraformaldehyde were placed in a 300-mL four necked flask under nitrogen flow, and 23.7 g (218 mmol) of trimethylsilyl chloride was added dropwise in an ice bath. The mixture was stirred for 1 hour, 35.6 g of methanol was then added dropwise, and the mixture was stirred for 1 hour. The organic phase was washed with 300 mL of saturated sodium hydrogen carbonate aqueous solution, and the obtained aqueous phase was further washed with 200 g of dichloromethane. A mixed solution of the two organic phases was further washed with 170 g of brine, and the obtained organic phase was dried over magnesium sulfate. The magnesium sulfate was removed by filtration, and the obtained dichloromethane solution was concentrated and dried to obtain the target compound [DM-2] (16.2 g, 33.1 mmol, yield: 91.0%).

The structure of the compound [DM-2] was confirmed from the following spectral data obtained by $^1$H-NMR analysis.

$^1$H-NMR (CDCl$_3$): δ 6.33 (d, 2H J=17.2), 6.20-6.14 (m, 2H), 5.96 (d, 2H J=10.4), 4.63 (s, 4H), 4.33 (m, 4H), 4.27 (m, 4H), 3.16-3.14 (br, 10H), 1.47 (m, 4H), 1.20 (m, 4H).

Synthesis Example 1

100.0 g of methyl methacrylate (MMA), 11.1 g of 2-hydroxyethyl methacrylate (HEMA), and 5.6 g of azobis(isobutyronitrile) (AIBN) as a polymerization catalyst were dissolved in 450.0 g of propylene glycol monomethyl ether (PGME), and a reaction was caused at 80° C. for 20 hours to obtain an acrylic copolymer solution (solid content concentration: 20% by mass) (P1). The obtained acrylic copolymer had a Mn of 4,200, and a Mw of 7,600.

<Production of Base Film>

An acrylic film used as a base material was produced by the following process. Specifically, raw material pellets formed of copolymers including methyl methacrylate as a main component was melted at 250° C. by an extruder, passed through a T-die, a casting roll and a drying roll, to produce an acrylic film having a thickness of 40 μm.

Examples 3 and 4 and Comparative Example 1

Components (A) to (E) and a solvent were mixed in each composition shown in Table 1, and the amount of the solvent to be added was adjusted so that the solid content concentration of the final composition was 5% by mass. Thus, each cured film-forming composition in Examples 3 and 4 and Comparative Example was prepared. For the obtained compositions, the orientation sensitivity, the patterning property, and adhesion were evaluated. A composition ratio in Table 1 represents a ratio in a solid content.

TABLE 1

| | (A) Component | | (B) Component | | (C) Component | | (D) Component | | (E) Component | | | |
|---|---|---|---|---|---|---|---|---|---|---|---|---|
| | Type | Mixing amount (part by mass) | Type | Mixing amount (part by mass) | Type | Mixing amount (part by mass) | Type | Mixing amount (part by mass) | Type | Mixing amount (part by mass) | Solvent | Solid content concentration (% by mass) |
| Example 3 | CIN 1 | 100 | P1 | 100 | HMM | 100 | DM-1 | 50 | PTSA | 9 | PGME | 5 |
| Example 4 | CIN 1 | 100 | P1 | 100 | HMM | 100 | DM-2 | 50 | PTSA | 9 | PGME | 5 |
| Comparative Example 1 | CIN 1 | 100 | P1 | 100 | HMM | 100 | | | PTSA | 8 | PGME | 5 |

[Evaluation of Orientation Sensitivity]

Each cured film-forming composition of Examples and Comparative Example was applied to the acrylic film by a bar coater, and heated and dried at 100° C. for 2 minutes in a heat circulation oven, to form a cured film. Each cured film was vertically irradiated with a linearly polarized light of 313 nm to form an orientation material. A polymerizable liquid crystal solution for horizontal orientation RMS03-013C, available from Merck Ltd., was applied onto the orientation material on a substrate by a bar coater, and then heated and dried at 70° C. for 60 seconds on a hot plate, to form a coating film having a film thickness of 1.0 μm. The coating film on this substrate was exposed at 300 mJ/cm$^2$ to produce a retardation material. The produced retardation material on the substrate was sandwiched between a pair of polarizing plates, expression situation of retardation properties in the retardation material was observed. The exposed amount of polarized UV light that was necessary for the orientation material to exhibit liquid crystal orientation properties was considered as the orientation sensitivity. The evaluation results are shown in Table 2.

[Evaluation of Patterning Properties]

Each cured film-forming composition of Examples and Comparative Example was applied to the acrylic film by a bar coater, and heated and dried at 100° C. for 1 minute in a heat circulation oven, to form a cured film. This cured film was vertically irradiated with a linearly polarized light of 313 nm at 20 mJ/cm$^2$ through a line-and-space mask of 350 μm. Next, the mask was removed, a substrate was rotated 90 degrees, and then vertically irradiated with linearly polarized light of 313 nm at 10 mJ/cm$^2$, to obtain an orientation material in which two liquid crystal orientation regions having different orientation controlling directions of liquid crystal by 90 degrees were formed. A polymerizable liquid crystal solution for horizontal orientation RMS03-013C, available from Merck Ltd., was applied onto the orientation material on the substrate by a bar coater, and then heated and dried at 70° C. for 60 seconds on a hot plate, to form a coating film having a film thickness of 1.0 μm. The coating film on this substrate was exposed at 300 mJ/cm$^2$ to produce a patterned retardation material in which two regions having different retardation properties were regularly arranged. The patterned retardation material on the substrate was observed by a polarized light microscope. The retardation material in which a retardation pattern was formed without orientation failure was evaluated as "○," and the retardation material in which orientation failure was observed was evaluated as "x." The evaluation results are shown in Table 2.

[Evaluation of Adhesion]

Each cured film-forming composition of Examples and Comparative Example was applied to the acrylic film by a bar coater, and heated and dried at 100° C. for 1 minute in a heat circulation oven, to form a cured film. This cured film was vertically irradiated with a linearly polarized light of 313 nm at 20 mJ/cm$^2$ through a line-and-space mask of 350 μm. Next, the mask was removed, a substrate was rotated 90 degrees, and vertically irradiated with linearly polarized light of 313 nm at 10 mJ/cm$^2$, to obtain an orientation material in which two liquid crystal orientation regions having different orientation controlling directions of liquid crystal by 90 degrees were formed. A polymerizable liquid crystal solution for horizontal orientation RMS03-013C, available from Merck Ltd., was applied onto the orientation material on the substrate by a bar coater, and then heated and dried at 70° C. for 60 seconds on a hot plate, to form a coating film having a film thickness of 1.0 μm. The coating film on this substrate was exposed at 300 mJ/cm$^2$ to produce a patterned retardation material in which two regions having different retardation properties were regularly arranged.

The patterned retardation material was incised at vertical and horizontal intervals of 1 mm with a 5×5 grid by a cutter. A cellophane tape peel test was carried out on this incised material. The evaluation results are listed in columns of "Initial." The retardation material in which any of 25 squares were not peeled and all remained was evaluated as "○", and the retardation material in which even one square was peeled was evaluated as "x." The evaluation results are shown in Table 2.

[Evaluation of Adhesion Durability]

The retardation material on the acrylic film produced in the same manner as in the evaluation of adhesion described above was placed in an oven set to a temperature of 80° C. and a humidity of 90%, and allowed to stand for 72 hours or more. The retardation material was then taken out, and the adhesion was evaluated in the same manner as in the evaluation of adhesion described above. The evaluation results are listed in columns of "durability," and shown in Table 2.

[Results of Evaluation]

The results of the evaluations are shown in Table 2 as described above.

TABLE 2

| | Orientation Sensitivity (mJ/cm$^2$) | Patterning | Adhesion Initial | Durability |
|---|---|---|---|---|
| Example 3 | 10 | ○ | ○ | ○ |
| Example 4 | 10 | ○ | ○ | ○ |
| Comparative Example 1 | 10 | ○ | ○ | x |

The exposed amounts of polarized UV light that was necessary for the orientation material to exhibit liquid crystal orientation properties of the orientation materials obtained using the cured film-forming compositions of Examples 3 and 4 were all as low as 10 mJ/cm$^2$, similar to the orientation material obtained using the cured film-forming composition of Comparative Example, and exhibited good orientation sensitivity.

The orientation materials obtained using the cured film-forming compositions of Examples 3 and 4 exhibited good patterning properties, similarly to the orientation material obtained using the cured film-forming composition of Comparative Example.

Even when the cured films obtained using the cured film-forming compositions of Examples 3 and 4 were treated at high temperature and high humidity, high adhesion was maintained. The cured films exhibited good adhesion durability.

In contrast, it was difficult to maintain the initial adhesion of the cured film obtained using the cured film-forming composition of Comparative Example after the cured film was treated at high temperature and high humidity.

As confirmed from Examples and Comparative Example, the compound of the present invention has an effect of improving the adhesion durability of the cured film-forming composition, and does not influence properties such as patterning properties.

INDUSTRIAL APPLICABILITY

When the compound of the present invention is added to a resin composition, a photosensitive resin such as a photoresist, or a coating using thermal crosslinkability or optical crosslinkability used in fields of displays such as televisions using a liquid crystal panel, and semiconductors, the performance of obtained cured film or the like can be improved. Therefore, the compound of the present invention is useful as an additive that does not influence properties such as transparency, or the like.

The invention claimed is:
1. An acrylic or methacrylic compound having N-alkoxyalkyl group, of Formula [1]:

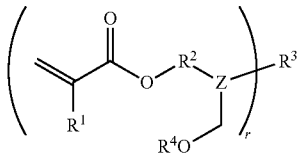

[1]

where
R$^1$ is a hydrogen atom or methyl group;
R$^2$ is a C$_{2-20}$ alkylene group, a divalent group consisting of a C$_{5-6}$ aliphatic ring, or a divalent aliphatic group containing a C$_{5-6}$ aliphatic ring, the group optionally containing an ether bond in its structure and the alkylene group being optionally linear or branched;
R$^3$ is an r-valent C$_{2-20}$ aliphatic group, an r-valent group consisting of a C$_{5-6}$ aliphatic ring, or an r-valent aliphatic group containing a C$_{5-6}$ aliphatic ring, the group optionally containing an ether bond in its structure and the r-valent C$_{2-20}$ aliphatic group being optionally linear or branched;
R$^4$ is a C$_{1-20}$ alkyl group, a monovalent group consisting of a C$_{5-6}$ aliphatic ring, or a monovalent aliphatic group containing a C$_{5-6}$ aliphatic ring, the group optionally containing an ether bond in its structure and the alkyl group being optionally linear or branched;
Z is >NCOO— or —OCON< where "-" is a bond, ">" and "<" each have two bonds, and any one of ">" and "<" is bonded to —CH$_2$OR$^4$; and
r is a natural number of 2 or more and 9 or less.
2. The compound according to claim 1, wherein
R$^2$ is a C$_{2-10}$ alkylene group, a divalent group consisting of a C$_{5-6}$ aliphatic ring, or a divalent aliphatic group containing a C$_{5-6}$ aliphatic ring, the group optionally containing an ether bond in its structure and the alkylene group being optionally linear or branched;
R$^3$ is an r-valent C$_{2-10}$ aliphatic group, an r-valent group consisting of a C$_{5-6}$ aliphatic ring, or an r-valent aliphatic group containing a C$_{5-6}$ aliphatic ring, the group optionally containing an ether bond in its structure and the r-valent C$_{2-20}$ aliphatic group being optionally linear or branched;
R$^4$ is a linear or branched C$_{1-6}$ alkyl group; and
r is 2 to 6.
3. The compound according to claim 1, wherein R$^4$ is methyl group, ethyl group, n-propyl group, or n-butyl group.
4. The compound according to claim 1, wherein R$^2$ is ethylene group.
5. The compound according to claim 1, wherein R$^3$ is n-hexylene group and r is 2.
6. A method for producing an acrylic or methacrylic compound having N-alkoxyalkyl group of Formula [1]:

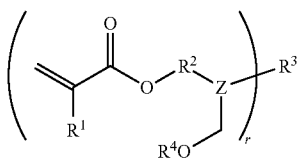

[1]

where
R$^1$, R$^2$, R$^3$, R$^4$, and r each have the meanings described below, Z is >NCOO— or —OCON<(where "-" is a bond, ">" and "<" each have two bonds, and any one of ">" and "<" is bonded to —CH$_2$OR$^4$), comprising reacting a compound of Formula (A):

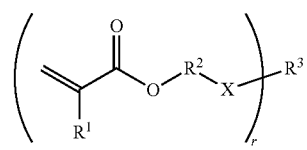

(A)

where
R$^1$ is a hydrogen atom or methyl group;
R$^2$ is a C$_{2-20}$ alkylene group, a divalent group consisting of a C$_{5-6}$ aliphatic ring, or a divalent aliphatic group containing a C$_{5-6}$ aliphatic ring, the group optionally containing an ether bond in its structure and the alkylene group being optionally linear or branched;
R$^3$ is an r-valent C$_{2-20}$ aliphatic group, an r-valent group consisting of a C$_{5-6}$ aliphatic ring, or an r-valent aliphatic group containing a C$_{5-6}$ aliphatic ring, the group optionally containing an ether bond in its structure and the r-valent C$_{2-20}$ aliphatic group being optionally linear or branched;
X is —NHCOO— or —OCONH—; and
r is a natural number of 2 or more and 9 or less;
with paraformaldehyde and trimethylsilyl chloride, and reacting the product with an alcohol compound of Formula (G):

R$^4$—OH where
R$^4$ is a C$_{1-20}$ alkyl group, a monovalent group consisting of a C$_{5-6}$ aliphatic ring, or a monovalent aliphatic group containing a C$_{5-6}$ aliphatic ring, the group optionally containing an ether bond in its structure and the alkyl group being optionally linear or branched.
7. The method according to claim 6, wherein
R$^2$ is a C$_{2-10}$ alkylene group, a divalent group consisting of a C$_{5-6}$ aliphatic ring, or a divalent aliphatic group containing a C$_{5-6}$ aliphatic ring, the group optionally containing an ether bond in its structure and the alkylene group being optionally linear or branched;
R$^3$ is an r-valent C$_{2-20}$ aliphatic group, an r-valent group consisting of a C$_{5-6}$ aliphatic ring, or an r-valent aliphatic group containing a C$_{5-6}$ aliphatic ring, the group optionally containing an ether bond in its structure and the r-valent C$_{2-20}$ aliphatic group being optionally linear or branched;
R$^4$ is a linear or branched C$_{1-6}$ alkyl group; and
r is 2 to 6.
8. The method according to claim 6, wherein R$^4$ is methyl group, ethyl group, n-propyl group, or n-butyl group.
9. The method according to claim 6, wherein R$^2$ is ethylene group.
10. The method according to claim 6, wherein R$^3$ is n-hexylene group and r is 2.

* * * * *